United States Patent [19]

Kadowaki

[11] 4,014,927
[45] Mar. 29, 1977

[54] PROCESS FOR PRODUCTION OF UNSATURATED ACIDS FROM CORRESPONDING UNSATURATED ALDEHYDES

[75] Inventor: Koju Kadowaki, Ami, Japan

[73] Assignee: Mitsubishi Petrochemical Company Limited, Japan

[22] Filed: Aug. 31, 1973

[21] Appl. No.: 393,469

[30] Foreign Application Priority Data

Sept. 7, 1972 Japan .............................. 47-89921
Dec. 5, 1972 Japan ............................ 47-121876
July 5, 1973 Japan .............................. 48-75886

[52] U.S. Cl. .......................... 260/530 N; 252/456; 252/464; 252/468; 252/469; 252/470
[51] Int. Cl.$^2$ ........................................ C07C 51/32
[58] Field of Search ................... 260/530 N, 533 N; 252/456

[56] References Cited

UNITED STATES PATENTS 3,567,772   3/1971   Yanagita et al. .............. 260/530 N

FOREIGN PATENTS OR APPLICATIONS 746,202   8/1970   Belgium ......................... 260/530 N

*Primary Examiner*—Vivian Garner
*Attorney, Agent, or Firm*—Robert E. Burns; Emmanuel J. Lobato; Bruce L. Adams

[57] ABSTRACT

A process for the production of unsaturated acids by catalytic oxidation of the corresponding unsaturated aldehydes in the presence of molybdenum-vanadium-iron based catalysts at a temperature of from 200° C to 400° C.

3 Claims, No Drawings

PROCESS FOR PRODUCTION OF UNSATURATED ACIDS FROM CORRESPONDING UNSATURATED ALDEHYDES

BACKGROUND OF THE INVENTION

There have been known a great variety of catalysts for use in producing unsaturated acids by vapor phase catalytic oxidation of the corresponding unsaturated aldehydes.

U.S. Pat. No. 3,567,773 discloses molybdenum-tungsten-vanadium based catalysts which are known to be especially effective. Also, German Patent No. 2,038,763 discloses molybdenum-vanadium-antimony based catalysts.

These catalysts may produce considerably good results. When these catalysts are to be used for industrial purpose, large amounts of the uniform catalysts are required. However, it is very difficult to produce such catalysts in such large amounts. In addition, further improvement in catalyst life is desirable, and even a slight improvement in yield is advantageous.

SUMMARY OF THE INVENTION

The applicants have made many studies on the abovementioned problems and, as a result, they have found that a new type of catalyst having a low specific area which is produced by adding silica or silica and alkali to a catalyst consisting of molybdenum, vanadium, iron and oxygen and processing the mixture under particular conditions provides excellent results. They have also discovered that a catalyst consisting of molybdenum, vanadium, iron and oxygen and containing added thereto at least one member selected from the group consisting of aluminum, titanium, rubidium, cobalt, zirconium, indium, zinc, niobium, tantalum, thallium, chromium, manganese, nickel and germanium provides excellent results.

It is accordingly an object of the present invention to provide a process for the production of unsaturated acids from the corresponding unsaturated aldehydes with good yield.

It is another object of the present invention to provide a catalyst having a long serviceable life which is suitable for use in producing unsaturated acids from the corresponding unsaturated aldehydes.

It is a further object of the present invention to provide a process for the production of a catalyst suitable for use in producing unsaturated acids from the corresponding unsaturated aldehydes.

A catalyst according to the present invention can be represented by the following empirical formula:

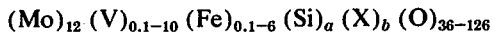

$(Mo)_{12} (V)_{0.1-10} (Fe)_{0.1-6} (Si)_a (X)_b (O)_{36-126}$ wherein $a$ is 0–24, $b$ is 0–3.0, $a$ plus $b$ is 0.1–27, and X is at least one element selected from the group consisting of Al, Ti, Rb, Co, Zr, In, Zn, Nb, Ta, Tl, Cr, Mn, Ni, Ge, Na and K.

PREFERRED EMBODIMENT OF THE INVENTION

In the case where silica is present in the catalyst according to the present invention, silica is preferably present in amounts such that the atomic ratio of silica to molybdenum is in the range of 0.2:12 to 24:12, and it is necessary to subject a homogeneous mixture of catalyst-raw-materials to evaporation to dryness at a temperature of from 90° C to 150° C or a spray drying at a temperature of from 100° C to 500° C, and to subject the dried mixture to heat treatment at a temperature of from 280° C to 450° C to provide a catalyst having a specific surface area of from 0.1 m²/g to 8 m²/g. The catalyst so produced preferably has a composition such that the atomic ratio of vanadium to molybdenum is in the range of 0.5:12 to 6:12 and the atomic ratio of iron to molybdenum is in the range of 0.25:12 to 3:12. Component X which is Na, K and/or Rb is present in amounts such that the atomic ratio of X to molybdenum is in the range of 0:12 – 2:12, and preferably, 0.1:12 to 1.8:12. Oxygen is present in amounts such that the atomic ratio of oxygen to molybdenum is in the range of 36:12 to 110:12.

In accordance with the present invention, it has been found that silica exhibits peculiar effects when it is added to the catalyst. In the past, silica has been widely used as a carrier for a catalyst in the form of silica gel or silica sol. In this case, the silica is used as a diluent for catalytically effective components or as a catalytic activity promoting agent due to its high specific surface area.

On the other hand, according to the present invention silica is combined with molybdenum, vanadium, iron and oxygen in the catalyst, and accordingly the specific surface area of the catalyst is extremely small. Such catalysts possessing a low specific surface area are highly stable in operation and provide improved selectivity to unsaturated aliphatic acids. In the case where alkali metals such as sodium, potassium, rubidium or the above-mentioned metals such as aluminum, titanium, cobalt co-exisist in the catalyst, the selectivity to unsaturated aliphatic acids is further increased.

In accordance with the present invention, a catalyst containing no silica may be prepared by any of the methods well known to those skilled in the art. The process for the production of the catalyst according to the present invention is illustrated by the following illustrative example.

A solution of ammonium metavanadate in an aqueous solution of ammonium molybdate is mixed with an aqueous solution of ferric nitrate, and to the mixture is added an oxide or a salt, of aluminum, titanium, rubidium, cobalt, zirconium, indium, zinc, niobium, tantalum, thallium, chromium, manganese, nickel or germanium and further, if desired, any suitable carrier such as silica. The resulting mixture is then evaporated to dryness. The solid cake so produced is pulverized and shaped. The shaped products are heat treated in the presence of air at a temperature of about 400° C for 5 hours.

Methods of producing improved catalysts possessing a low specific surface area wherein silicon or silicon and alkali are present therein include an evaporation to dryness method, an impregnation method, and the like. The evaporation to dryness method is particularly preferable, and among others a spray drying method is most preferable. This method will now be described.

Aqueous solutions respectively of ammonium molybdate, ammonium metavanadate, ferric nitrate and water glass are mixed, and, if desired, together with an aqueous solution of salts of the above-mentioned metal elements such as aluminum, titanium niobium, and tantalum. The mixture is then evaporated or vaporized to dryness. When the starting aqueous solutions are mixed, there may possibly be deposited precipitation, but it is preferable to bring the mixture into a solution or a colloidal solution, if possible. The resulting mixture solution is concentrated. Deposition of hetrogenous precipitation during concentration must be avoided. For this reason, the solution should be maintained at a temperature of from 90 to 150° C, depending on the catalyst composition. For this purpose, in some cases the solution is evaporated to dryness under pressure.

If the evaporation to dryness method is substituted by the spray drying method, a catalyst possessing a low specific surface area can be more easily produced. Any suitable spray dryer such as, for example, of rotating disc type, pressure nozzle type, and two-fluid nozzle type spray dryers may be used. Hot air may be supplied either concurrently or countercurrently. When spray drying is carried out, the solid content of the starting mixture solution is preferably in the range of 5 to 70%, and in particular of 15 to 60%. If required, the starting mixture solution may be partially pre-concentrated before it is subjected to the spray drying. The temperature of the starting mixture solution to be supplied to the spray dryer is from room temperature to 100° C. The inlet temperature of hot air varies depending upon operation conditions, and it is, suitably, from 100° C to 500° C and in particular from 130° C to 450° C. A outlet temperature above 70° C of hot air is satisfactory.

The content of free water in the dried solid must be not greater than 10% and preferably not greater than 4%. The evaporated or spray dried solids so obtained are, if necessary, further dried at a temperature of from 100° C to 200° C for several hours to 24 hours and then pulverized. To the powder are added lubricants and the like and the mixture is pressed into pellets.

The pellets obtained are calcined. The temperature of calcination is a most important factor and is preferably between 280° C and 450° C, and particularly from 300° C to 420° C. Temperatures below 280° C result in no adequate formation of effective active components, while temperatures above 450° C may cause undesirable phenomena such as decomposition of the active components and increasing of specific surface area.

A catalyst containing silicon thus obtained possesses a low specific surface area of 0.1 m²/g to 8 m²/g as measured according to the BET method.

The effects of silicon may be exhibited irrespective of whether the above-mentioned metal elements such as aluminum, titanium, niobium, tantalum and alkali (sodium, potassium, or rubidium) are present or are not present. The catalyst used in the process of the present invention may also be supported on conventional carriers such as alumina and silicon carbide.

As the starting materials useful for the production of the catalyst, molybdenum materials include ammonium molybdate, molybdenum trioxide, molybdic acid and the like; vanadium materials include ammonium metavanadate, vanadium pentoxide and the like; and iron materials include ferric nitrate, ferric chloride and the like. The metal elements such as aluminum, titanium, niobium, tantalum are used in the form of the oxides, nitrates, chlorides and the like. As a source of silicon, silicates, water glass, colloidal silica and the like may be used. Alkali materials as a source of alkali may be used in the form of the nitrates, halides, hydroxides or the salts of molybdic acid, metavanadic acid, silicic acid and the like.

For the production of unsaturated acids by vapor phase catalytic oxidation of the corresponding unsaturated aldehydes using the catalyst formed in the aforementioned procedure, a gaseous mixture of unsaturated aldehyde and oxygen or oxygen containing gas (for example, air) and, if desired, steam is passed over the catalyst maintained at a temperature of from 200° C to 400° C. From the reaction mixture the product is recovered by a conventional method known to those skilled in the art, and the resulting unsaturated acids are separated from the recovered product.

The molar ratio of oxygen to unsaturated aldehyde in the gaseous feed mixture is preferably from 0.2:1 to 3:1. Suitable unsaturated aldehydes used in the process of the present invention are acrolein and methacrolein. A gaseous mixture resulting from oxidation of propylene or isobutylene may be also used herein. The reaction may be advantageously carried out at approximately atmospheric pressure because of the convenience of operation. If desired, the reaction may be conducted under increased or reduced pressures, which pressures range from 0.5 atmosphere absolute to 10 atmospheres absolute.

The contact time of the gaseous mixture with the catalyst is suitably from 0.4 to 10 seconds.

The process of the present invention is further illustrated by the following examples. In the examples, the terms conversion, selectivity and yield are defined as follows:

$$\text{Conversion (percent)} = \frac{\text{Moles of unsaturated aldehyde converted}}{\text{Moles of unsaturated aldehyde fed}} \times 100$$

$$\text{Selectivity (percent)} = \frac{\text{Moles of unsaturated acid obtained}}{\text{Moles of unsaturated aldehyde converted}} \times 100$$

$$\text{Yield (percent)} = \frac{\text{Moles of unsaturated acid obtained}}{\text{Moles of unsaturated aldehyde fed}} \times 100$$

EXAMPLE 1

85.0 parts by weight of ammonium paramolybdate (parts referred to hereinafter are by weight), 14.1 parts of ammonium metavanadate and 16.2 parts of ferric nitrate were each dissolved in 500 parts, 500 parts and 50 parts of distilled water, respectively, and all of the foregoing solutions were mixed. To the resulting mixture, after it was maintained at 85° C for 10 minutes while stirring, were added 177 parts of aqueous silica sol containing 20% by weight of silica and 5.35 parts of zirconyl nitrate. The resulting slurry was then evaporated to dryness and further dried at 180° C for 16 hours. The solid cake formed was pulverized and pressed into pellets. These catalyst pellets were heat treated in the presence of air at 390° C for 5 hours.

The composition of the catalyst so obtained was represented by the following formula:

$$Mo_{12}V_3Fe_1Zr_{0.5}$$

This catalyst was placed in a reactor tube. A gaseous mixture of 5% acrolein, 4% oxygen, 30% steam and 61% nitrogen, the percentage being by volume, was passed over the catalyst during a contact time of 3.6 seconds at a temperature of 295° C.

The result of the reaction was as follows:

|  | Percent |
|---|---|
| Conversion of acrolein | 96.0 |

| | Percent |
|---|---|
| Selectivity to acrylic acid | 94.1 |
| Yield of acrylic acid | 90.4 |

Examples 2 – 7

Various catalysts were prepared by the procedure described in Example 1 except that 1.56 parts of aluminum hydroxide, 1.60 parts of titanium oxide, 2.97 parts of rubidium nitrate, 5.85 parts of cobalt nitrate, 7.10 parts of indium nitrate or 5.95 parts of zinc nitrate were respectively substituted for 5.35 parts of zirconyl nitrate.

Another series of runs were made employing these catalysts under the conditions set forth in Example 1 except that the reaction temperatures were varied.

The catalysts, reaction temperatures, and results are shown in Table 1.

Table 1

| Example No. | Catalyst composition | Reaction temperature, °C | Percent conversion of acrolein | Percent selectivity to acrylic acid | Percent yield of acrylic acid |
|---|---|---|---|---|---|
| 2 | $Mo_{12}V_3Fe_1Al_{0.5}$ | 260 | 99.0 | 90.1 | 89.3 |
| 3 | $Mo_{12}V_3Fe_1Ti_{0.5}$ | 290 | 95.0 | 96.1 | 91.4 |
| 4 | $Mo_{12}V_3Fe_1Rb_{0.5}$ | 270 | 97.0 | 93.0 | 90.3 |
| 5 | $Mo_{12}V_3Fe_1Co_{0.5}$ | 270 | 95.1 | 92.6 | 88.0 |
| 6 | $Mo_{12}V_3Fe_1In_{0.5}$ | 295 | 95.5 | 94.6 | 90.5 |
| 7 | $Mo_{12}V_3Fe_1Zn_{0.5}$ | 265 | 97.0 | 91.3 | 88.5 |

EXAMPLES 8 – 9

A gaseous feed consisting of 5% metacrolein, 3.5% oxygen, 30% steam and 61.5% nitrogen (the percent is by volume) was passed over each of the catalysts prepared in Examples 2 and 3 during a contact time of 3.6 seconds at temperatures of 310° C and 279° C, respectively.

The results of these reactions are shown in Table 2.

Table 2

| Example No. | Catalyst composition | Reaction temperature °C | Percent conversion of metacrolein | Percent selectivity to methacrylic acid | Percent yield of methacrylic acid |
|---|---|---|---|---|---|
| 8 | $Mo_{12}V_3Fe_1Al_{0.5}$ | 279 | 33.3 | 65.4 | 21.8 |
| 9 | $Mo_{12}V_3Fe_1Ti_{0.5}$ | 310 | 51.3 | 58.8 | 30.2 |

EXAMPLE 10

Into a solution of 85.0 parts of ammonium paramolybdate in 500 parts of distilled water was added 14.1 parts of ammonium metavanadate, and the ammonium metavanadate was dissolved with heating.

8.1 parts of ferric nitrate and 3.56 parts of indium nitrate were each dissolved in 50 parts and 25 parts of distilled water, respectively, and these two solutions were added to the foregoing solution. To the resulting mixture was added 178 parts of aqueous silica sol containing 20% by weight of silica, and the resulting slurry was evaporated to dryness with thorough stirring. After drying at 150° C for 16 hours, the solid cake formed was pulverized and pressed into pellets. The catalyst pellets were heat treated in the presence of air at 400° C for 5 hours. The composition of the catalyst so obtained was represented by the following formula:

$$Mo_{12}V_3Fe_{0.5}In_{0.25}$$

This catalyst was placed in a reactor tube. A gaseous mixture of 5% acrolein, 5% oxygen, 20% steam and 70% nitrogen (the percentage is by volume) was passed over the catalyst for a contact time of 1.8 seconds at a temperature of 277° C.

The results of the reaction were as follows.

| Reaction time (hour) | Percent conversion of acrolein | Percent selectivity to acrylic acid | Percent yield of acrylic acid |
|---|---|---|---|
| 24 | 95.6 | 93.4 | 89.4 |
| 4320 | 96.0 | 94.0 | 90.2 |

EXAMPLE 11

72.0 parts of molybdenum trioxide and 11.3 parts of vanadium pentoxide were dissolved in 150 parts of a 28% aqueous ammonia, and the solution was increased to 1200 parts with the addition of distilled water. To the resulting mixture were added two solutions of 16.8 parts of ferric nitrate and 3.11 parts of zinc nitrate each in 50 parts of distilled water, and further 1.67 parts of titanium oxide and 180 parts of aqueous silica sol containing 20% by weight of silica. The resulting slurry was evaporated to dryness with thorough stirring. After drying at 180° C for 16 hours, the solid cake formed was pulverized and pressed into pellets. The catalyst pellets formed were heat treated in the presence of air at 390° C for 5 hours. The composition of this catalyst was represented by the following formula:

$$Mo_{12}V_3Fe_1Zn_{0.25}Ti_{0.5}$$

The catalytic oxidation of acrolein using this catalyst was carried out according to the procedure described in Example 1 except that the reaction temperature was 285° C.

The result of the reaction was as follows:

| | Percent |
|---|---|
| Conversion of acrolein | 97.5 |
| Selectivity to acrylic acid | 90.7 |
| Yield of acrylic acid | 88.5 | except that the reaction temperatures were varied. The catalysts, reaction temperatures, and results are shown in Table 3.

Table 3

| Example No. | Catalyst Composition | Reaction temperature °C | Percent conversion of acrolein | Percent selectivity to acrylic acid | Percent yield of acrylic acid |
|---|---|---|---|---|---|
| 13 | $Mo_{12}V_3Fe_1Zr_{0.3}Rb_{0.35}$ | 310 | 95.0 | 95.1 | 90.3 |
| 14 | $Mo_{12}V_3Fe_1Zr_{0.3}Co_{0.3}$ | 290 | 96.0 | 93.5 | 89.8 |
| 15 | $Mo_{12}V_3Fe_1Zr_{0.3}Zn_{0.2}$ | 280 | 97.0 | 92.8 | 90.0 |

EXAMPLE 12

14.1 parts of ammonium metavanadate was dissolved in a solution of 85.0 parts of ammonium paramolybdate in 800 parts of distilled water. The ammonium metavanadate was brought into solution with heating. To the solution were added two solutions of 16.2 parts of ferric nitrate and 3.21 parts of zirconyl nitrate each in 50 parts of distilled water. To the resulting mixture was added 178 parts of aqueous silica sol containing 20% by weight of silica and the resulting slurry was thoroughly stirred. After a solution of 3.56 parts of indium nitrate in 25 parts of distilled water was added thereto, the slurry was evaporated to dryness and dried at 150° C for 16 hours. The solid cake firmed was pulverized and pressed into pellets. The catalyst pellets obtained were heat treated in the presence of air at 385° C for 5 hours. The composition of this catalyst was represented by the following formula:

$$Mo_{12}V_3Fe_1Zr_{0.3}In_{0.25}$$

This catalyst was placed in a reactor tube. A gaseous mixture of 5% acrolein, 4% oxygen, 20% steam and 71% nitrogen (the percentage is by volume) was passed over the catalyst for a contact time of 3.6 seconds at a temperature of 300° C. The result of the reaction was as follows:

| | Percent |
|---|---|
| Conversion of acrolein | 95.0 |
| Selectivity to acrylic acid | 95.4 |
| Yield of acrylic acid | 90.6 |

EXAMPLES 13 – 15

Various catalysts were prepared according to the procedure described in Example 12 except that 2.08 parts of rubidium nitrate, 3.50 parts of cobalt nitrate or 2.39 parts of zinc nitrate was respectively substituted for 3.56 parts of indium nitrate.

Another series of runs was carried out, employing these catalysts under the conditions in Example 12

EXAMPLE 16

85.0 parts by weight of ammonium paramolybdate (parts referred to hereinafter being by weight), 14.1 parts of ammonium metavanadate and 16.2 parts of ferric nitrate were each dissolved in 500 parts, 500 parts and 50 parts of distilled water, respectively, and all of the foregoing solutions were mixed. To the resulting mixture, after it was maintained at 85° C for 10 minutes with stirring, were added 177 parts of aqueous silica sol containing 20% by weight of silica and 2.66 parts of niobium pentoxide. The resulting slurry was then evaporated to dryness and further dried at 180° C for 16 hours. The solid cake formed was pulverized and pressed into pellets. The catalyst pellets were heat treated in the presence of air at 370° C for 5 hours.

The composition of this catalyst was represented by the following formula:

$$Mo_{12}V_3Fe_1Nb_{0.5}$$

The catalyst was placed in a reactor tube. A gaseous mixture of 5% acrolein, 4% oxygen, 30% steam and 61% nitrogen (the percentage is by volume) was passed over the catalyst with a contact time of 3.6 seconds at a temperature of 285° C.

The result of the reaction was as follows:

| | Percent |
|---|---|
| Conversion of acrolein | 97.0 |
| Selectivity to acrylic acid | 94.2 |
| Yield of acrylic acid | 91.4 |

EXAMPLES 17 – 22

Various catalysts were prepared according to the procedure described in Example 16 except that 2.76 parts of tantalum, 5.33 parts of thallous nitrate, 8.00 parts of chromium nitrate, 5.74 parts of manganese nitrate, 5.82 parts of nickel nitrate or 2.09 parts of germanium oxide was respectively substituted for 2.66 parts of niobium pentoxide.

Another series of runs was carried out, employing these catalysts under the conditions in Example 12 except that the reaction temperatures were varied. The catalysts, reaction temperatures and results are shown in Table 4.

Table 4

| Example No. | Catalyst composition | Reaction temperature °C | Percent conversion of acrolein | Percent selectivity to acrylic acid | Percent yield of acrylic acid |
|---|---|---|---|---|---|
| 17 | $Mo_{12}V_3Fe_1Ta_{0.5}$ | 275 | 97.5 | 92.7 | 90.4 |
| 18 | $Mo_{12}V_3Fe_1Tl_{0.5}$ | 280 | 96.9 | 93.9 | 91.0 |
| 19 | $Mo_{12}V_3Fe_1Cr_{0.5}$ | 270 | 99.2 | 92.2 | 91.5 |
| 20 | $Mo_{12}V_3Fe_1Mn_{0.5}$ | 280 | 97.2 | 92.4 | 89.8 |
| 21 | $Mo_{12}V_3Fe_1Ni_{0.5}$ | 285 | 98.0 | 93.2 | 91.3 |
| 22 | $Mo_{12}V_3Fe_1Ge_{0.5}$ | 270 | 96.5 | 93.3 | 90.0 |

EXAMPLES 23 – 24

A gaseous feed consisting of 5% methacrolein, 3.5% oxygen, 30% steam and 61.5% nitrogen (the percentage is by volume) was passed over the respective catalysts prepared in Examples 2 and 3 at a contact time of 3.6 seconds at temperatures of 295° C and 290° C, respectively. The results of these reactions are shown in Table 5.

Table 5

| Example No. | Catalyst composition | temperature °C | Percent conversion methacrolein | Percent selectivity methacrylic acid | Percent methacrylic acid |
|---|---|---|---|---|---|
| 23 | $Mo_{12}V_3Fe_1Nb_{0.5}$ | 295 | 38.1 | 66.2 | 25.2 |
| 24 | $Mo_{12}V_3Fe_1Cr_{0.5}$ | 290 | 35.4 | 64.7 | 22.9 |

EXAMPLE 25

14.1 parts of ammonium metavanadate was added in a solution of 85.0 parts of ammonium paramolybdate in 500 parts of distilled water. The ammonium metavanadate was dissolved with heating. Two solutions of 8.1 parts of ferric nitrate and 2.87 parts of manganese nitrate each in 50 parts and 25 parts of distilled water were added to the foregoing solution. To the resulting mixture was added 178 parts of aqueous silica sol containing 20% by weight of silica and the resulting slurry was evaporated to dryness with thorough stirring. After drying at 150° C for 16 hours, the solid cake formed was pulverized and pressed into pellets. The catalyst pellets were heat treated in the presence of air at 400° C for 5 hours. The composition of this catalyst was represented by the following formula:

$$Mo_{12}V_3Fe_{0.5}Mn_{0.25}$$

The catalyst was placed in a reactor tube. A gaseous mixture of 5% acrolein, 5% oxygen, 20% steam and 70% nitrogen (the percentage is by volume) was passed over the catalyst with a contact time of 1.8 seconds at a temperature of 280° C. The result of the reaction was as follows:

| Reaction time (hr) | Percent conversion of acrolein | Percent selectivity to acrylic acid | Percent yield of acrylic acid |
|---|---|---|---|
| 48 | 97.5 | 93.3 | 91.0 |
| 7680 | 98.5 | 92.8 | 91.4 |

EXAMPLE 26

72.0 parts of molybdenum trioxide and 11.3 parts of vanadium pentoxide were dissolved in a 28% aqueous ammonium hydroxide solution and the solution was brought up to 1200 parts with the addition of distilled water. To the resulting solution were added two solutions of 16.8 parts of ferric nitrate and 4.18 parts of chromium nitrate each in 50 parts of distilled water, and further 1.39 parts of niobium pentoxide and 180 parts of aqueous silica sol containing 20% by weight of silica. The resulting slurry was evaporated to dryness with thorough stirring. After drying at 180° C for 16 hours, the solid cake formed was pulverized and pressed into pellets. The catalyst pellets were heat treated in the presence of air at 350° C for 2 hours. The composition of this catalyst was represented by the following formula:

$$Mo_{12}V_3Fe_1Cr_{0.25}Nb_{0.25}$$

The catalytic oxidation of acrolein using this catalyst was carried out according to the procedure described in Example 1 except that the reaction temperature was 275° C.

The result of the reaction was as follows:

|  | Percent |
|---|---|
| Conversion of acrolein | 98.0 |
| Selectivity to acrylic acid | 92.6 |
| Yield of acrylic acid | 90.7 |

EXAMPLE 27

14.1 parts of ammonium metavanadate was added to a solution of 85.0 parts of ammonium paramolybdate in 800 parts of distilled water. The ammonium metavanadate was dissolved by heating. 16.2 parts of ferric nitrate, 2.87 parts of manganese nitrate and 4.0 parts of chromium nitrate were each dissolved in 50 parts of distilled water, and all of these solutions were added to the foregoing solution. To the mixture was then added 178 parts of aqueous silica sol containing 20% by weight of silica and thoroughly mixed. The resulting slurry was evaporated to dryness and dried at 130° C for 16 hours. The solid cake formed was pulverized and pressed into pellets. The catalyst pellets were heat treated in the presence of air at 370° C for 5 hours. The composition of this catalyst was represented by the following formula:

$Mo_{12}V_3Fe_1Mn_{0.25}Cr_{0.25}$

This catalyst was placed in a reactor tube. A gaseous mixture of 5% acrolein, 4% oxygen, 20% steam and 71% nitrogen (the percentage is by volume) was passed over the catalyst with a contact time of 3.6 seconds at a temperature of 280° C.

The result of the reaction was as follows:

|  | Percent |
| --- | --- |
| Conversion of acrolein | 96.4 |
| Selectivity to acrylic acid | 94.8 |
| Yield of acrylic acid | 91.4 |

EXAMPLES 28 – 30

Various catalysts were prepared by the same procedure described in Example 27 except that 1.33 parts of niobium pentoxide, 2.67 parts of thallous nitrate or 1.05 parts of germanium oxide was substituted for 4.00 parts of chromium nitrate.

Another series of runs was carried out, employing these catalysts under the conditions in Example 27 except that the reaction temperatures were varied. The catalysts, reaction temperatures and results are shown in Table 6.

Table 6

| Example No. | Catalyst composition | Reaction temperature °C | Percent conversion of acrolein | Percent selectivity to acrylic acid | Percent yield of acrylic acid |
| --- | --- | --- | --- | --- | --- |
| 28 | $Mo_{12}V_3Fe_1Mn_{0.25}Nb_{0.25}$ | 275 | 96.1 | 94.7 | 91.0 |
| 29 | $Mo_{12}V_3Fe_1Mn_{0.25}Tl_{0.25}$ | 280 | 97.5 | 93.1 | 90.8 |
| 30 | $Mo_{12}V_3Fe_1Mn_{0.25}Ge_{0.25}$ | 280 | 96.7 | 93.0 | 89.9 |

EXAMPLE 31

85.0 parts of ammonium paramolybdate, 14.1 parts of ammonium metavanadate and 16.2 parts of ferric nitrate were each dissolved in 200 parts, 500 parts and 20 parts of distilled water, respectively, and all of the foregoing solutions were mixed. To the resulting mixture were added 144 parts of aqueous colloidal silica sol containing 20% by weight of silica with $Na_2O$ content of less than 0.02% by weight. The resulting slurry was charged in an autoclave furnished with a pressure regulating valve, a stirrer, and a steam jacket and evaporated to dryness at an internal temperature of from 110° C to 115° C to obtain a glassy solid. After drying at 160° C for 12 hours, the solid was pulverized and pressed into pellets. The catalyst pellets was heated to 380° C at a raising speed of 17° C/min. and at that temperature heat treated for 5 hours. The composition of this catalyst was represented by the following formula:

$Mo_{12}V_3Fe_1Si_{12}$

The atomic ratio of sodium to molybdenum was 0.03 or less : 12, and the catalyst had a specific surface area of 2.6 m²/gr.

The catalyst was placed in a reactor tube. A gaseous mixture of 5% acrolein, 5% oxygen, 30% steam and 60% nitrogen was passed over the catalyst with a contact time of 2 seconds at a temperature of 280° C.

The result of the reaction was as follows:

|  | Percent |
| --- | --- |
| Conversion of acrolein | 95.4 |
| Selectivity to acrylic acid | 92.4 |
| Selectivity to acetic acid | 2.1 |
| Yield of acrylic acid | 88.1 |

EXAMPLE 32

85.0 parts of ammonium paramolybdate, 14.1 parts of ammonium metavanadate, 8.08 parts of ferric nitrate and 2.04 parts of sodium nitrate were each dissolved in 200 parts, 500 parts, 20 parts and 10 parts of distilled water, respectively, and all of the foregoing solutions were mixed. To the resulting mixture was added 180 parts of aqueous colloidal silica sol containing 20% by weight of silica with $Na_2O$ content of less than 0.02% by weight. The resulting slurry was heated while thoroughly stirring. When the insoluble matters disappeared in the mixture maintained at a temperature of 102° C, the mixture was evaporated to dryness at a temperature above 102° C. During the process of evaporation, neither precipitation nor crystallization occurred, and the mixture was gradually changed into a concentrated solution in the form of millet jelly and finally into a glassy solid.

Thereafter, the solid was treated by the procedure described in Example 31 to provide a catalyst. The composition of this catalyst was represented by the following formula:

$Mo_{12}V_3Fe_{0.5}Si_{15}Na_{0.6}$

The catalyst possessed a specific surface of 2.4 m²/g.

The catalytic oxidation of acrolein using this catalyst was carried out according to the procedure described in Example 31 except that the reaction temperature was 300° C.

The result of the reaction was as follows:

|  | Percent |
| --- | --- |
| Conversion of acrolein | 96.0 |
| Selectivity to acrylic acid | 94.2 |
| Yield of acrylic acid | 90.4 |

EXAMPLE 33

85 parts of ammonium paramolybdate was dissolved in 500 parts of distilled water at about 60° C, and into this solution was dissolved 18.8 parts of ammonium metavanadate. Then, two solutions of 32.3 parts of ferric nitrate and 3 parts of potassium chloride each in 40 parts and 20 parts of distilled water were added to the foregoing solution and mixed together. To the resulting mixture was added 180 parts of aqueous colloidal silica containing 0.02% by weight of silica with Na₂O content of less than 0.02% by weight. Thereafter, the resulting slurry was treated by the procedure described in Example 32 to provide a catalyst. The composition of the catalyst was represented by the following formula:

$$Mo_{12}V_4Fe_2Si_{15}K_1$$

The catalyst possessed a specific surface area of 3.7 m²/gr.

The catalytic oxidation of acrolein using this catalyst was carried out under the conditions in Example 31 except that the reaction temperature was 280° C.

The result of the reaction was as follows:

|  | Percent |
|---|---|
| Conversion of acrolein | 96.2 |
| Selectivity to acrylic acid | 94.5 |
| Yield of acrylic acid | 90.9 |

EXAMPLE 34

85.4 parts of ammonium paramolybdate, 14.1 parts of ammonium metavanadate, 16.2 parts of ferric nitrate and 0.97 parts of rubidium chloride were each dissolved in 200 parts, 500 parts, 20 parts and 10 parts of distilled water, respectively, and all of the foregoing solutions were mixed. To the resulting mixture was added 180 parts of aqueous colloidal silica sol containing 20% by weight of silica with Na₂O content of less than 0.02% by weight. Thereafter, the resulting slurry was treated by the same procedure described in Example 31 to provide a catalyst. The composition of the catalyst was represented by the following formula:

$$Mo_{12}V_3Fe_1Si_{15}Rb_{0.2}$$

The catalyst possessed a specific surface area of 2.3 m²/gr.

The catalytic oxidation of acrolein using this catalyst was carried out under the conditions in Example 31.

The result of the reaction was as follows:

|  | Percent |
|---|---|
| Conversion of acrolein | 94.3 |
| Selectivity to acrylic acid | 94.4 |
| Yield of acrylic acid | 89.0 |

EXAMPLE 35

69.1 parts of molybdenum trioxide and 3.64 parts of vanadium pentoxide were each dissolved in 200 parts of a warm aqueous solution containing NH₄OH at about 60° C and 12.1 parts of ferric nitrate was dissolved in 20 parts of distilled water, and all of the foregoing solutions were mixed. To the resulting mixture was added 96 parts of aqueous colloidal silica containing 20% by weight of silica with Na₂O content of less than 0.02% by weight. Thereafter, the resulting slurry was treated by the procedure described in Example 31 to provide a catalyst.

The composition of the catalyst was represented by the following formula:

$$Mo_{12}V_1Fe_{0.75}Si_8$$

The atomic ratio of sodium to molybdenum was 0.02 or less : 12. The catalyst possessed a specific surface area of 4.8 m²/gr.

The catalytic oxidation of acrolein employing the catalyst was carried out under conditions in Example 31.

The result of the reaction was as follows:

|  | Percent |
|---|---|
| Conversion of acrolein | 94.8 |
| Selectivity to acrylic acid | 92.2 |
| Yield of acrylic acid | 87.4 |

EXAMPLE 36

85.0 parts of ammonium paramolybdate, 14.1 parts of ammonium metavanadate and 8.08 parts of ferric nitrate were each dissolved in 200 parts, 500 parts of 20 parts of distilled water, respectively, and all of the foregoing solutions were mixed. To the resulting mixture was added a diluted solution of 19 parts of an aqueous solution containing 6.8 percent weight of Na₂O and 25.3 percent weight of SiO₂ in 100 parts of distilled water. This solution was intimately mixed with stirring, boiled and concentrated to a solid content of about 40%. The resulting slurry was spray-dried by means of a spray dryer manufactured by NIRO CO. (a rotating disc type, concurrent style). The inlet temperature of hot air was 270° C, while the outlet temperature thereof was 110° C. To the resulting fine powder was added graphite in an amount of 2% by weight based on the powder and the mixed powder was pressed into pellets. Following shaping, the catalyst pellets obtained were heated to 380° C at a raising speed of 17° C/min and at that temperature heat treated for 5 hours.

The composition of the catalyst was represented by the following formula:

$$Mo_{12}V_3Fe_{0.5}Si_2Na_1$$

The catalyst possessed a specific surface area of 0.72 m²/g.

The catalyst was placed in a reactor tube. A gaseous mixture of 5% acrolein, 5% oxygen, 30% steam and 60% nitrogen was passed over the catalyst with a contact time of 2 seconds at a temperature of 305° C.

The result of the reaction was as follows:

|  | Percent |
|---|---|
| Conversion of acrolein | 97.4 |
| Selectivity to acrylic acid | 96.6 |
| Selectivity to acetic acid | 1.1 |
| Yield of acrylic acid | 94.1 |

EXAMPLE 37

85.0 parts of ammonium paramolybdate, 14.1 parts of ammonium metavanadate and 16.2 parts of ferric nitrate were each dissolved in 200 parts, 500 parts and 20 parts of distilled water, respectively, and all of the foregoing solutions were mixed. To the resulting mixture was added 144 parts of aqueous colloidal silica containing 20% by weight of silica with Na₂O content of less than 0.02% by weight and the resulting slurry was condensed to a liquid content of about 25%. The slurry so formed was spray-dried by means of the spray dryer as described in Example 36. The inlet and outlet temperatures of hot air were 280° C and 115° C, respectively.

The resulting powder was heat treated in air at a temperature of 350° C for 2 hours, and the treated powder was supported on a silica-alumina carrier (Macroport SA 52 05, manufactured by Norton Co.) in amounts such that the catalyst components comprised 30% by weight of the catalytic composite. The resulting catalytic composite was heat treated in air at 350° C for 2 hours to provide the final catalytic composite.

The composition of the catalyst components was represented by the following formula:

$$Mo_{12}V_3Fe_1Si_{12}$$

The atomic ratio of sodium to molybdenum was 0.03 or less : 12. The catalyst possessed a specific surface area of 0.68 m²/gr.

The catalytic oxidation of acrolein using the catalytic composite was carried out under the conditions in Example 36 except that the reaction temperature was 290° C.

The result of the reaction was as follows:

|  | Percent |
|---|---|
| Conversion of acrolein | 96.8 |
| Selectivity to acrylic acid | 95.9 |
| Yield of acrylic acid | 92.8 |

EXAMPLE 38

A catalyst was prepared by the procedure described in Example 36 except that a diluted solution of 23.1 parts of an aqueous solution containing 8.3% by weight of $K_2O$ and 20.8% by weight of $SiO_2$ in 100 parts of distilled water was substituted for the diluted solution containing 6.8% by weight of $Na_2O$ and 25.3% by weight of $SiO_2$.

The composition of the catalyst was represented by the following formula:

$$Mo_{12}V_3Fe_1Si_2K_1$$

The catalyst possessed a specific surface area of 0.85 m²/g.

The catalytic oxidation of acrolein using this catalyst was carried out under the conditions in Example 36 except that the reaction temperature was 300° C.

The result of the reaction was as follows:

|  | Percent |
|---|---|
| Conversion of acrolein | 96.7 |
| Selectivity to acrylic acid | 95.8 |
| Yield of acrylic acid | 92.6 |

EXAMPLE 39

85.0 parts of ammonium paramolybdate, 14.1 parts of ammonium metavanadate, 16.2 parts of ferric nitrate and 0.97 parts of rubidium chloride were each dissolved in 200 parts, 500 parts, 20 parts and 10 parts of distilled water, respectively, and all of the foregoing solutions were mixed. To the resulting mixture was added 180 parts of aqueous colloidal silica containing 20% by weight of silica with $Na_2O$ content of less than 0.02% by weight. Thereafter, the resulting slurry was treated according to the same procedure described in Example 36.

The composition of the catalyst was represented by the following formula:

$$Mo_{12}V_3Fe_1Si_{15}Rb_{0.2}$$

The catalyst possessed a specific surface area of 0.97 m²/gr.

The catalytic oxidation of acrolein using this catalyst was carried out under the conditions in Example 36 except that the reaction temperature was 300° C.

The result of the reaction was as follows:

|  | Percent |
|---|---|
| Conversion of acrolein | 95.2 |
| Selectivity to acrylic acid | 95.6 |
| Yield of acrylic acid | 91.0 |

EXAMPLE 40

400 parts of ammonium molybdate was dissolved in 2000 parts of distilled water while heating, and into this solution was dissolved 66 parts of ammonium metavanadate. An aqueous solution of 76 parts of ferric nitrate in 200 parts of distilled water was added to the foregoing solution and thereto was further added an aqueous solution of 25.2 parts of water glass (No. 1) in 120 parts of distilled water.

The resulting solution was concentrated to a solid content of about 37%. The concentrated solution so formed was spray dried by means of the spray dryer described in Example 36. The inlet and outlet temperatures of hot air were 280° C and 115° C, respectively. The resulting catalyst powder was heat treated in air at a temperature of 350° C for 2 hours.

The composition of the catalyst was represented by the following formula:

$$Mo_{12}V_3Fe_1Si_{0.8}Na_{0.8}$$

The catalyst possessed a specific surface area of 0.60 m²/gr.

The catalyst powder was supported on the Macroport SA 5205 carrier in amounts such that the catalyst components comprised 30% by weight of the catalytic composite.

The catalytic oxidation of acrolein using this catalytic composite was carried under the conditions in Example 36.

The result of the reaction was as follows:

|  | Percent |
|---|---|
| Conversion of acrolein | 97.4 |
| Selectivity to acrylic acid | 96.4 |
| Yield of acrylic acid | 93.9 |

EXAMPLE 41

A catalyst was prepared by the same procedure described in Example 40 except that two solutions of 2.87 parts of manganese nitrate and 4.0 parts of chromium nitrate each in 50 parts of distilled water were further added.

The composition of the catalyst was represented by the following formula:

$$Mo_{12}V_{13}Fe_1Mn_{0.25}Cr_{0.25}Si_{0.8}Na_{0.8}$$

The catalyst possessed a specific surface area of 0.65 m²/gr.

The catalyst powder was supported on the Macroport SA 5205 carrier in amounts such that the catalyst components comprised 30% by weight of the catalytic composite.

The catalytic oxidation of acrolein using this catalytic composite was carried out under the conditions in Example 36 except that the reaction temperature was 280° C.

The result of the reaction was as follows:

|  | Percent |
|---|---|
| Conversion of acrolein | 99.2 |
| Selectivity to acrylic acid | 96.8 |
| Yield of acrylic acid | 96.0 |

What we claim is:

1. A process for the production of unsaturated acids by the vapor-phase catalytic oxidation of the corresponding unsaturated aldehyde selected from the group consisting of acrolein and methacrolein at a temperature of 200°–400° C. in the presence of a catalyst consisting essentially of molybdenum vanadium, iron silicon, element X and oxygen represented by the formula $$(Mo)_{12}(V)_{0.5-6}(Fe)_{0.25-3}(Si)_{0.2-24}(X)_{0-2}(O)_{36-110},$$

wherein X is at least one element selected from the group consisting of Na, K and Rb, and has a specific surface of 0.1 m²/g to 8 m²/g, and the catalyst is prepared by drying a homogenous aqueous solution or slurry mixture of the catalyst-raw-materials by evaporation to dryness or spray drying and calcining the dried product thus obtained at a temperature of from 280° C to 450° C.

2. A process according to claim 1 wherein said aqueous solution mixture is evaporated at a temperature of from 90° C to 150° C without deposition of heterogenous precipitates during evaporation.

3. A process according, to claim 1 wherein said drying process is conducted by spraying said mixture in hot air at a temperature of from 100° C to 500° C.

* * * * *